US00PP18860P3

(12) United States Plant Patent
Benardella

(10) Patent No.: US PP18,860 P3
(45) Date of Patent: Jun. 3, 2008

(54) ROSE PLANT NAMED 'BENUNO'

(50) Latin Name: *Rosa hybrida*
Varietal Denomination: BENuno

(75) Inventor: Frank Benardella, Englishtown, NJ (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 289 days.

(21) Appl. No.: 11/263,669

(22) Filed: Oct. 31, 2005

(65) Prior Publication Data

US 2007/0101468 P1 May 3, 2007

(51) Int. Cl.
*A01H 5/00* (2006.01)

(52) U.S. Cl. ..... Plt./132

(58) Field of Classification Search ..... Plt./130, Plt./132
See application file for complete search history.

*Primary Examiner*—Kent Bell

(57) ABSTRACT

'BENuno' is a new and distinct rose with hybrid tea-type, exhibition form flowers of a unique near-white blend. Flowers are born one to a stem and last well over a week as cut flowers. Fragrance is moderate. The thick foliage has shown very good disease resistance in national, outside testing. 'BENuno' is well suited as a garden perennial, a large container plant and for cut flowers.

1 Drawing Sheet

Genus and species: *Rosa hybrida.*
Varietal denomination: 'BENuno'.

CROSS REFERENCE

'JACecond', U.S. Plant Pat. No. 11,369. The pollen parent for this new invention was used in other successful crosses in this breeding program. Perhaps the one most closely resembling this new invention is 'BENpete', not patented. 'BENpete' has hybrid tea-type, exhibition form flowers, similar to those on this new invention. The new invention has near white flowers flushed with pink. 'BENpete' has predominately red flowers with the base and reverse of the petals being white. The blooms on 'BENpete' are ½-inch smaller and generally have more petals but have been noted at times to have similar petal counts to this new invention. Both plants are upright growing: 'BENpete' is taller while this new invention is a bit more compact and has stronger stems. 'BENpete' is more apt to have multiple flowers per stem. Both cultivars offer good disease resistance. The foliage of 'BENpete' is smaller and darker green while on this new invention they are closer together on the stems.

RIGHTS TO THE INVENTION

Be it known that Frank A. Benardella of Englishtown, N.J., claims invention of new and useful improvements in ROSE PLANT/var. 'BENuno' and following is a clear and exact description of the same.

BACKGROUND OF THE INVENTION

This present invention relates to a new and distinct variety of hardy, bush type rose plant. This new variety is a single seedling created by Frank A. Benardella under controlled conditions in a greenhouse in Englishtown, N.J., by crossing the following rose plants: an unnamed, unintroduced seedling created within the hybridizing program as the seed parent and 'JACecond', U.S. Plant Pat. No. 11,369 as the pollent parent.

The primary goal of this breeding program is to produce unique roses with award winning, hybrid tea form on plants having favorable attributes that will increase public appeal. To achieve this goal roses are selected for this hybridizing program primarily for their award winning, hybrid tea form. Pertaining to this particular cross, both parents were noted for their exhibition, hybrid tea form flowers that are borne one to a stem. The pollen parent, 'JACecond', is noted for its good disease resistance.

The seed parent was a seedling that was created through a series of crosses within this breeding program. Its miniature, yellow blend blooms did have hybrid tea, exhibition form. The plant habit was miniature and compact. This new invention is a larger flowered miniflora with white blend blooms.

The pollen parent, 'JACecond' is a red flowered hybrid tea rose, making the first and most noticeable difference from this new invention to be the color of the flowers. 'JACecond' is also about two feet taller and wider with larger flowers than this new invention. Traits acquired explicitly from 'JACecond' are the quantity and shape of the prickles and strong and upright plant habit.

Asexual reproduction by cuttings of this new variety in Englishtown, N.J., and Arroyo Grande, Calif., show that all distinguishing characteristics of this new cultivar continually come true to form.

SUMMARY OF THE INVENTION

The present invention relates to a new and distinct variety of vigorous, hardy, bush-type rose plant with primarily white, exhibition, hybrid tea-form flowers. This invention is distinguished from other white rose cultivars of which I am aware by the combination of its petal count, size of bud, full open bloom and reflex to the petals, lasting time for flowers on the plant and as cut flowers plus plant size and habit. The average petal count for this new invention is 23 to 26. The open bloom size is 3½ to 3⅝ inches across and 1¼ inch deep. The bud has a diameter of 9/16 inch with a height of 15/16 inch. Flowers last an average of 7 days on the plant and 9 to 12 days or more as cut flowers. Petals have only a slight and gradual reflex. The plant grows upright to an average height of 3 feet and width of about 2 feet.

The new invention is further characterized by:

Flowers primarily borne one to a strong stem;

Dark green, semi-glossy foliage;

Good Disease resistance;

Moderate, sweet fragrance;

Suitability for production from softwood cuttings in pots;

A plant that grows and flowers well in all climates, both in the greenhouse and outdoors, providing decoration in the garden as a perennial or in containers and is excellent for cut flowers.

BRIEF DESCRIPTION OF THE DRAWING

There are three photographs in the accompanying drawing. The two larger photographs were taken in October of flowers and stems taken from plants grown in Arroyo Grande, Calif., under plastic, under greenhouse conditions. Both of these photographs were taken inside under artificial lighting. The top one shows buds and flowers of this new invention in all stages of development as well as young and old foliage. The large lower photograph shows a flowering stem, typical leaves and prickles. The smaller inset photograph, taken outdoors in light shade in the spring, shows a profile view of a flower at exhibition stage from a plant of this new invention as grown under glass in a greenhouse in Englishtown, N.J.

BOTANICAL DESCRIPTION OF THE PLANT

Following is a detailed description pertaining specifically to this new and distinct variety of rose plant as observed at around 4 years of age after having been grown under plastic in Arroyo Grande, Calif., in soiless mix on a constant feed program, in 8 to 10 inch nursery containers. All major colour plate identifications made are referring to The Royal Horticultural Society Colour Chart except where common terms of definition are employed.

FLOWERS

Blooming habit: Repeat bloomer with around 35 days between bloom cycles.

Borne: Singly; occasionally one or two smaller buds will grow from the nodes immediately below the terminal flower on the flowering stem.

Bud: Form is ovate, having a rounded base and acuminate apex. The diameter at its widest point is around 9/16 inch and the height is around 15/16 inch. The color when the sepals first divide is near 145C, a medium yellow-green.

Sepals: There are five sepals that extend beyond the tip of the bud by 7/16 to 8/16 inch. The shape of the two outermost sepals is lanceolate, one having a foliated attenuate apex and one having a foliated lanceolate apex. The three innermost sepals are ovate-lanceolate with subulate apices having no foliar appendages. The outside surfaces of these extensions from the apex of the sepals as well as the foliar appendages are dark green, near 137A, and flushed with near 187A from the Greyed-Purple group. The rest of the outside surface of the sepals is a dark green, between 137B and 146B, with the basal area and point of attachment to the receptacle sometimes being near 146B or 146C, from the Yellow-Green group. The color of the inside surface of the extensions from the apex and the foliar appendages is a dark green, near 139A. The rest of the inside surface is covered with a fine pubescence, giving it the appearance of near 193B–D, from the Greyed-Green group. The base of all sepals is truncate at the union with the receptacle. The outer two sepals are usually ¼ inch wide but one is usually ⅛ inch longer than the other, varying from 1⅛ to 1⅜ inches long. All three innermost sepals are usually 5/16 inch wide but length can vary from 13/16 inch to 1⅛ inches.

The outer surface is matte and there are stipitate glands present. The two outermost sepals have only a couple of single hairs and many stipitate glands. The margins of these two outermost sepals are lined with stipitate glands and one or two foliar appendages along each. The outer surface of the two innermost sepals have many stipitate glands and hairs that increase toward the margins to the point of being downy along the edges and with ciliate margins. The sepal in-between is a combination of the outer and inner, with characteristics evenly divided along the main vein. The three innermost sepals all have soft prickles on their central vein. The sepals roll back with the petals until they are perpendicular to the receptacle, remaining thus until the petals drop, and then rolling back to the peduncle and remaining attached in this position while the hips form.

Bloom: When fully expanded the blooms measure 3½ to 3⅝ inches across and 1¼ inch deep. The upper profile remains flat from when the bud first opens until the petals drop. The lower profile is cupped when the flower first starts to open and becomes flattened convex by the time the bloom is fully expanded.

Petalage: There are 23 to 26 petals and 2 to 8 petaloids. The medium thick petals are overlapping. They last an average of 7 days on the plant and 9 to 12 days or more as cut flowers, before detaching cleanly from the receptacle. The fragrance is moderate and sweet, fruity.

Petals: Both surfaces of the petals are satiny and glabrous. The shape of the outer petals is broad oblanceolate to broad fan-shaped and becoming deltoid when mature. Intermediate petals are obcordate and inner, young petals are rounded. The apex is truncate with a sinuate margin that becomes increasingly sinuate with age. The width of the outermost petals varies from 1½ to 1 9/16 inches and the length varies from 1 5/16 to 1 7/16 inches.

When the flower first opens, the outer petals are an off white, a color somewhat lighter than that between 159D, from the orange white group, and 19D, Egyptian Buff, and flushed lightly with a color nearest 36C, Orient Pink, first around the outer edges and increasing and deepening as the petals reflex and are exposed to sunlight. The basal area is a very light Primrose Yellow, near 4D, and a little darker, near 4B at the point of attachment. The reverse of the outer petals is overall lighter, near 159D, with the basal area nearest 13D and the point of attachment near 4D. The inner petals at the center of the flower are nearest 158D, from the Yellow-White group, right down to the point of attachment that is light Primrose Yellow, near 4C. The reverse of the inner petals is also near 158D down to the point of attachment, which is near 4D.

When full blown all petal surfaces are somewhat lighter than near 158D from the Yellow-White group with reflexed upper surfaces being lightly flushed with Neyron Rose, near 55B. Point of attachments have become near 2D, from the Yellow group, and basal areas of outer petals is near 2C.

There is little change as the flower fades with only the basal areas and points of attachment becoming lighter, both becoming nearest 4D on both sides of the outer petals except near 2D for the basal area of the inside of the outer petals.

The general tonality is slightly off-white with a pink blush. Tonality from a distance is white with a pink blush.

Petaloids: The color and texture of the petaloids is the same as the inner petals. The size is extremely variable, from long and narrow to short and wide. Width varies from ¼ inch to 9/16 inch. The shortest length found on the observed plants is ⅝ inch and the longest found was on ones doubled over, measuring up to 1¼ inches when straightened out. All petaloids appear misshapen and incomplete, sometimes appearing torn. Margins become increasingly sinuate with maturity.

Peduncle: The diameter of the peduncles is ⅛ inch. Lengths are quite variable from 1¼ to 1 9/16 inches. If second blooms are produced from the nodes immediately beneath a terminal flower the peduncles are smaller with a diameter of only 3/32 inch and the length varying from 15/16 inch to 1¼ inches. The aspect is generally straight and they are very strong. Color is a medium yellow-green, near 146C, with no anthocyanin coloration present. The surface is glossy with numerous soft prickles up to ⅛ inch long and sometimes very small, 1/32 inch long, and sometimes no prickles but always glands and stipitate glands. There are no hairs near the juncture with the receptacle but they gradually increase to many hairs near the attachment to the stem. At the base of the peduncle there often is a small simple leaf, varying in size, and with stipules attached the entire length of the petiole.

Receptalce: The receptacle is funnel-shaped, measuring 5/16 inch at its widest part and 7/16 inch tall. Color is a medium yellow-green, nearest 146C. The surface is matte and glabrous. The top surface is circular, matte and glabrous, with a diameter of ⅜ inch and light yellow, near 2D.

REPRODUCTIVE ORGANS

Stamens, filaments and anthers are arranged regularly around the styles, attached to the outer rim of the receptacle. The average quantity is 92. Filaments are quite undulant and the length ranges from 7/16 to 9/16 inch. The lower half is near 4D, a very pale Primrose Yellow, and the upper half is near 55D, a medium pink. The color of the anthers is near 19D, Egyptian Buff. The color of the pollen is near 22B, Orange Buff.

Pistils, styles and stigmas are few in quantity, about 18. Styles are a medium thickness, have a slight curve and are about ¼ inch long on the mature flower. Their color is Rose Bengal, near 57C. The stigmas are white, closest to 158D from the Yellow-White group. There are no mature hips to observe at this time. Immature hips are globular.

PLANT

The plant of this new invention is uniformly branched with a very upright habit. The mature height is 3 feet and width is 20 to 24 inches. Foliage is pinnately compound, most often with five leaflets but sometimes with seven or three. Length of internodes is variable and random. On main stems length varies from 1 inch to 1⅝ inches. On lateral, nodes are further apart, ranging from 1 3/16 to 2 1/16 inches. There are usually five or six nodes on flowering stems, ranging from ⅝ inch to 1¼ inches, and often around mid-stem there are two or three that are equidistant.

Leaflets: The shape of the leaflets is elliptical with an oval base and often with an obtuse apex. Terminal leaflets have an acuminate base and apex. The size of the terminal leaflets ranges from 1⅛ to 1 5/16 inches wide and 1 1/16 to 1½ inches long. Anthocyanin coloring is weak on new leaflets, quickly disappearing, but strong on the petioles, rachis and veins. Color of new leaflets is near 144A, Lettuce Green, flushed light with near 181B from the Greyed-Red group. The undersurface is near 183D, from the Greyed-Purple group. Anthocyanin coloring is absent from the mature leaflets. The upper surface is dark green, near 139A, and the under surface is a little lighter, near 147B. The upper surface is semi-glossy and glabrous. The underside is matte, leathery and with the central vein protruding and primary laterals protruding slightly. Serration on the edge is simple with serratures becoming closer together towards the apex. There is a gland at the tip of each serrate.

Petioles: The diameter of the petiole is generally 1/16 inch but may be as large as 3/32 inch. The length varies from ½ to ⅞ inch. Color along the ridges on new growth is Oxblood Red, near 183C, and a little lighter, near 183D, in the groove. The underside is also near 183D. On mature leaves color along the ridges on the upper side is dark green, near 137A, and much lighter, near 145C from the Yellow-Green group, in the groove. The under side is medium green, near 146D from the Yellow-Green group. There are a few stipitate glands along the ridges on the upper side and some hairs in the groove with more at the junction with the petiolules to the basal leaflets. The underside is glabrous.

Rachis: The length of the rachis on five-leaflet leaves varies from 7/16 to ¾ inch. On a seven-leaflet leaf the length averages 1⅛ inches. Color along the ridges on the upper side on the mature leaf is dark green, near 147A from the Yellow-Green group, and somewhat lighter, near 146C, in the groove. The under surface is near 146B. There are several stipitate glands along the ridges and a few hairs in the groove, increasing in quantity at the juncture with the petiolules. The under side has one to three prickles and several stipitate glands.

Petiolules: Color of the petiolules on the young leaf is near 183D on both upper and lower surfaces. On the mature leaf color is near 146C in the groove and the ridge is between 146B and 147A. The underside is near 146D. The length varies from 2/32 to 3/32 inch and from 9/32 to 15/32 inch to terminal leaflets. The upper surface is glabrous. The under surface often has one gland or stipitate gland at the juncture with the rachis of small leaflets, and a tiny prickle at the juncture with the rachis of medium and large leaflets.

Stipules: Two stipules are at the base of each petiole as a nearly identical pair. They are attached on either side of the petiole for 13/32 to 14/32 inch and then angle out at about 75 degrees, on a flat plane, for 2/16 to 3/16 inch. The margins are somewhat sinuate and lined with stipitate glands. The color of the adaxial side is a little lighter than the adaxial surface of the leaflet, near 137B. The abaxial surface is the same as the abaxial side of the leaflet, near 147B.

Resistance: This new invention has good disease resistance to powdery mildew, balckspot and rust.

Wood: The diameter of the main stalks is 13/32 inch. The diameter of primary laterals is 9/32 inch and flowering stems is ⅛ to 3/16 inch. New wood is glabrous and near 147B from the Yellow-Green group. The color of the old wood is slightly more yellow, near 146C, also from the Yellow-Green group. Old wood has parallel rows of lenticels. Root initiation from new wood cuttings is 8 to 12 days under controlled greenhouse conditions.

Prickles: The prickles of this new invention angle down and are hooked downward with a gentle curve, some having the profile of a pelican's bill. The bases are linear and 3/32 inch wide. The quantity of prickles on the main stalk is none to three per inch of stem. These vary in size from 5/16 inch long on a base that is 11/16 inch long, to 3/16 inch long on a base that is 7/32 inch long, to 1/8 inch long on a base that is 1/8 inch long. On the laterals prickles are more apt to be a uniform 1/4 inch long on a base that is 5/16 inch long, often congregating below the nodes. On the flowering stems they also tend to congregate below the nodes and may be 3 to 6 per inch of stem or 21 to 32 on five inches of stem, most often having 22 per five inches of stem. When young, the color is a medium yellow-green, closest to 151A. When old, the color of the prickles is between 164B and 163C, both from the Greyed-Orange group.

Hardiness: This new invention has been tested for hardiness in zones 5 through 10 with winter protection recommended for zones 7 and below. Plants performed well in testing in American Horticultural Society heat zones 10 through 1.

It is claimed:

1. A new and distinct variety of hardy rose plant, substantially as herein shown and described, characterized particularly as to novelty by the uniquely colored, near-white blend flowers, having a moderate fragrance and borne primarily singly (one to a stem) on an upright and uniformly branched plant.

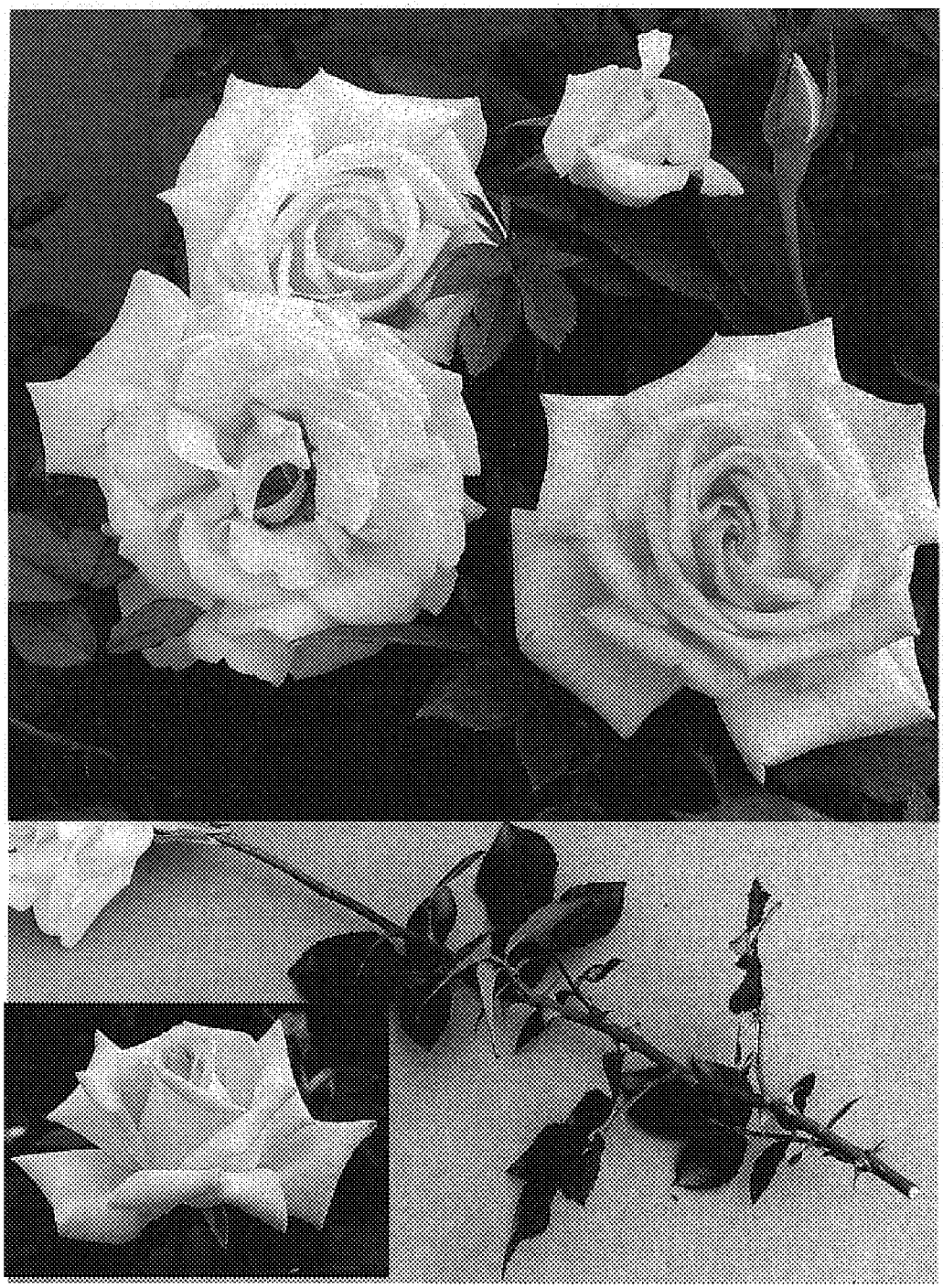

* * * * *